United States Patent
Simon

(10) Patent No.: US 6,245,322 B1
(45) Date of Patent: *Jun. 12, 2001

(54) FLUID COMPOSITION IN THE FORM OF AN OIL-IN-WATER EMULSION COMPRISING AN ACRYLIC TERPOLYMER AND ITS USES, IN PARTICULAR ITS COSMETIC USES

(75) Inventor: Pascal Simon, Vitry sur Seine (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/503,200

(22) Filed: Feb. 14, 2000

(30) Foreign Application Priority Data

Mar. 17, 1999 (FR) .................................................. 99 03319

(51) Int. Cl.[7] ................................ A61K 7/42; A61K 7/00
(52) U.S. Cl. ............................ 424/59; 424/401; 424/70.1
(58) Field of Search ................................ 424/59, 60, 400, 424/401; 514/844–846, 880

(56) References Cited

U.S. PATENT DOCUMENTS 6,060,041 * 5/2000 Candau et al. ......................... 424/59

FOREIGN PATENT DOCUMENTS

| 0 173 109 | 3/1986 | (EP) . |
| 0 250 943 | 1/1988 | (EP) . |
| 0 262 465 | 4/1988 | (EP) . |
| 0 388 582 | 9/1990 | (EP) . |
| 0 613 682 | 9/1994 | (EP) . |

* cited by examiner

Primary Examiner—Shelley A. Dodson
Assistant Examiner—Konata M. George
(74) Attorney, Agent, or Firm—Oblon, Spivak, McClelland, Maier & Neustadt, P.C.

(57) ABSTRACT

A fluid composition in the form of an oil-in-water emulsion comprising, in a physiologically acceptable medium, an oily phase dispersed in an aqueous phase and comprising up to 0.5% by weight of active material with respect to the total weight of the composition of at least one acrylic terpolymer obtained from a carboxylic acid comprising α,β-ethylenic unsaturation, from a non-surface-active monomer comprising ethylenic unsaturation other than (a), and from a non-ionic urethane monomer which is the reaction product of a monohydric non-ionic amphiphilic compound with an isocyanate comprising monoethylenic unsaturation. The composition may be used, for example, for caring for, removing make-up from, cleansing and/or scenting the skin, hair and/or lips. The composition may also be used for impregnating fabrics intended for cleansing and/or removing make-up from the skin, lips and/or eyes.

20 Claims, No Drawings

FLUID COMPOSITION IN THE FORM OF AN OIL-IN-WATER EMULSION COMPRISING AN ACRYLIC TERPOLYMER AND ITS USES, IN PARTICULAR ITS COSMETIC USES

BACKGROUND OF THE INVENTION

1. Field of the Invention

The present application relates to a fluid composition in the form of an oil-in-water emulsion comprising at least one acrylic terpolymer and to the use of the composition, in particular for caring for, removing make-up from, cleansing and/or scenting the skin of the body or the face, the hair and/or the lips and for impregnating fabrics intended for cleansing and/or removing make-up from the skin, lips and/or eyes.

2. Description of the Background

For various reasons related especially to a better comfort of use (softness, emollience and others), current cosmetic compositions are generally provided in the form of an emulsion of the oil-in-water (O/W) type composed of a continuous aqueous dispersing phase and of a non-continuous oily dispersed phase or of an emulsion of the water-in-oil (W/O) type composed of a continuous oily dispersing phase and of a non-continuous aqueous dispersed phase. O/W emulsions are in the greatest demand in the cosmetics field because they comprise an aqueous phase as an external phase, which confers on them, during application to the skin, a fresher, less greasy and lighter feel than W/O emulsions.

The emulsions are generally stabilized by appropriate emulsifying surfactants which, by virtue of their amphiphilic structure, become positioned at the oil/water interface and thus stabilize the dispersed droplets. However, these emulsifiers exhibit the disadvantage of being penetrating and potentially irritating to the skin, eyes and scalp, in particular for users with sensitive skin.

In addition, in these conventional emulsions which comprise emulsifying surfactants, the size of the oily globules is generally greater than several microns. Such emulsions can have inadequate cosmetic and physicochemical properties (oily feel, instability over time). Increasing the level of the surfactants does not generally solve the problems discussed above. The stability required is not always achieved and the cosmetic properties are not improved (waxy and heavy feel, lack of freshness on application). Furthermore, as indicated above, it is also inadvisable to use an excessively high level of surfactant for reasons of harmlessness.

A solution in order to achieve freedom from the phenomena of instability of O/W emulsions (creaming and phase separation) consists in adding thickening agents to the emulsion, the role of which thickening agents is to create, within the aqueous phase, a gelled matrix which serves to set the oily droplets and which provides for mechanical maintenance of the entire emulsion. However, this solution exhibits the disadvantage of not making it possible to obtain all the desired textures and in particular fluid and light textures which are readily and rapidly applied to the skin without leaving a residual film.

Furthermore, the replacement of the surfactants by polymers comprising, in their chain, a hydrophilic part and a hydrophobic part composed of a fatty chain, such as copolymers of $C_{10}$–$C_{30}$)alkyl acrylate and of acrylic or methacrylic acid, such as the product "Pemulen TR2" sold by Goodrich, has been envisaged. However, these polymers exhibit the disadvantage of not making it possible to obtain compositions which are sufficiently fluid to be able to be vaporized.

SUMMARY OF THE INVENTION

It is an object of the invention is to be able to prepare very fluid and stable oil-in-water emulsions which optionally do not comprise emulsifying surfactant conventionally used in O/W emulsions and which exhibit good cosmetic properties without having the disadvantages of compositions described above.

The Inventors have discovered, unexpectedly, a novel family of polymers allowing such emulsions to be produced.

These polymers make it possible to prepare oil-in-water emulsions over a wide range of viscosity and of content of oily phase which remain stable over time at room temperature or at higher temperatures.

Thus, the present invention thus relates to a fluid composition in the form of an oil-in-water emulsion comprising, in a physiologically acceptable medium, an oily phase dispersed in an aqueous phase, comprising up to 0.5% by weight of active material with respect to the total weight of the composition of at least one acrylic terpolymer obtained from (a) an $\alpha,\beta$-ethylenically unsaturated carboxylic acid, (b) a non-surface-active ethylenically unsaturated monomer other than (a), and (c) a non-ionic urethane monomer which is the reaction product of a monohydric non-ionic amphiphilic compound with a monoethylenically unsaturated isocyanate.

The present invention also relates to a method of caring for, removing make-up from, cleansing and/or scenting the skin, lips and/or hair, comprising applying the inventive composition to the skin, lips and/or hair.

The present invention also relates to a cleansing wipe comprising a fabric impregnated with the inventive composition.

The present invention also relates to a method of making the cleansing wipe of claim 17, comprising impregnating a fabric with the inventive composition.

The present invention also relates to a method of cosmetically treating the skin, hair and/or lips, comprising applying the inventive composition to the skin, hair and/or lips.

A more complete appreciation of the invention and many of the attendant advantages thereof will be readily obtained as the same becomes better understood by reference to the following detailed description.

DETAILED DESCRIPTION OF THE INVENTION

The composition obtained generally has a homogeneous texture which is pleasant on application while being stable on storage. Furthermore, it is very fluid. The viscosity of the emulsions generally ranges from 0.02 to 3 Pa·s, this viscosity being measured at approximately 25° C. using a "Rheomat 180" viscometer equipped with a 2 rotor. This range for the viscosity includes all specific values and subranges therebetween, such as 0.05, 0.1, 0.2, 0.5, 1 and 2 Pa·s.

The emulsion of the invention is advantageously devoid of surfactant conventionally used in O/W emulsions and it exhibits, for this reason, the advantage of not being irritating to particularly sensitive skin. In addition, this emulsion exhibits the advantage of making possible the incorporation of heat-sensitive active principles because it can be manufactured at room temperature, both in the stage of neutralization of the polymer and in the stage of dispersion of the oily phase.

The acrylic terpolymer used in accordance with the invention is soluble or swellable in alkaline substances. It is preferably characterized in that it comprises, with respect to the total weight of the terpolymer:

(a) Approximately 20 to 70% by weight, preferably 25 to 55% by weight, of a carboxylic acid comprising α,β-monoethylenic unsaturation. These ranges include all specific values and subranges therebetween, such as 30, 35, 45, 60 and 65% by weight;

(b) Approximately 20 to 80% by weight, preferably 30 to 65% by weight, of a non-surface-active monomer comprising monoethylenic unsaturation other than (a). These ranges include all specific values and subranges therebetween, such as 25, 35, 40, 45, 50, 60, 70 and 75% by weight; and (c) Approximately 0.5 to 60% by weight, preferably 10 to 50% by weight, of a non-ionic urethane monomer which is the reaction product of a monohydric non-ionic amphiphilic compound with an isocyanate comprising monoethylenic unsaturation. These ranges include all specific values and subranges therebetween, such as 1, 2, 5, 15, 25, 30, 40 and 55% by weight.

The carboxylic acid comprising α,β-monoethylenic unsaturation (a) can be chosen from numerous acids and in particular acrylic acid, methacrylic acid, crotonic acid, itaconic acid and maleic acid. It is preferably methacrylic acid. A large proportion of acid is preferable in order to give a polymer structure which dissolves and gives a thickening agent by reaction with an alkaline compound, such as sodium hydroxide, alkanolamines, aminomethylpropanol or aminomethylpropanediol.

The terpolymer comprises a monomer (b) comprising monoethylenic unsaturation which does not have a surface-active property and which is also preferably present in a high proportion, as indicated above. The preferred monomers are those which give water-insoluble polymers when they are homopolymerized and they are illustrated by $C_1$–$C_4$ alkyl acrylates and methacrylates, such as methyl acrylate, ethyl acrylate, butyl acrylate or the corresponding methacrylates. The more particularly preferred monomers are methyl acrylate and ethyl acrylate. Other monomers which can be used are styrene, vinyltoluene, vinyl acetate, acrylonitrile and vinylidene chloride. Nonreactive monomers are preferred, these monomers being those in which the only ethylenic group is the sole group which is reactive under the conditions of the polymerization. However, monomers which comprise groups which are reactive under the action of heat, such as hydroxyethyl acrylate, can optionally be used.

The monohydric non-ionic amphiphilic compounds used to obtain the non-ionic urethane monomer (c) are well known and are generally alkoxylated hydrophobic compounds comprising an alkylene oxide forming the hydrophilic part of the molecule. The hydrophobic compounds are generally composed of an aliphatic alcohol or of an alkylphenol, in which compounds a carbonaceous chain comprising at least six carbon atoms constitutes the hydrophobic part of the amphiphilic compound.

The preferred monohydric non-ionic amphiphilic compounds are compounds having the following formula (I):

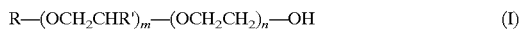

in which R is chosen from alkyl groups comprising from 6 to 30 carbon atoms and aralkyl groups comprising from 8 to 30 carbon atoms, R' is chosen from alkyl groups comprising from 1 to 4 carbon atoms, n is a mean number ranging from approximately 6 to 150 and m is a mean number ranging from approximately 0 to 50, provided that n is at least as great as m and that n+m=6 to 150.

Preferably, in the compounds of formula (I), the R group is chosen from alkyl groups comprising from 18 to 26 carbon atoms and alkylphenyl groups in which the alkyl part comprises 8 to 13 carbon atoms; the R' group is the methyl group; m=0 and n=6 to 150. The compound of formula (I) can be in particular an oxyalkylenated derivative, in particular an oxyethylenated derivative, of an aliphatic alcohol of vegetable origin and in particular of behenyl alcohol, the R radical in the formula (I) then being the behenyl radical.

The isocyanate comprising monoethylenic unsaturation used to form the non-ionic urethane monomer (c) can be chosen from highly varied compounds. Use may be made of a compound comprising any copolymerizable unsaturation, such as an acrylic, methacrylic or allylic unsaturation. The preferred isocyanate comprising monoethylenic unsaturation is α,α-dimethyl-m-isopropenylbenzyl isocyanate.

The acrylic terpolymer defined above is obtained by copolymerization in aqueous dispersion of the components (a), (b) and (c). The copolymerization may be accomplished according to conventional procedures, as disclosed in EP-A-0 173 109, incorporated herein by reference.

Examples of terpolymers which can be used according to the invention include the reaction product of methacrylic acid, as component (a), of ethyl acrylate, as component (b), and of a non-ionic urethane macromonomer having the following structure (II):

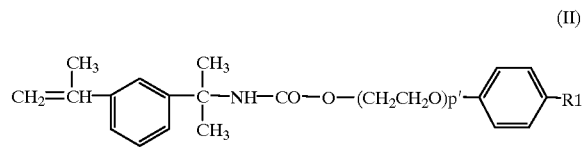

in which p' ranges from 6 to 150 and is preferably equal to 30 and R1 is chosen from alkyl radicals comprising from 8 to 13 carbon atoms, as described in Example 3 of the document EP-A-0 173 109, as component (c).

The preferred acrylic terpolymer used according to the invention is obtained from methacrylic acid, as component (a), from methyl acrylate, as component (b), and from a non-ionic urethane macromonomer having the following structure (III):

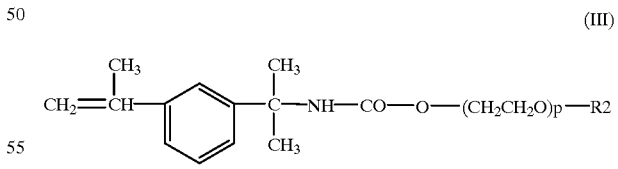

in which p ranges from 6 to 150 and R2 is chosen from linear alkyl radicals comprising from 18 to 26 and preferably from 20 to 24 carbon atoms, as component (c). The R2 radical in the compound of formula (III) is preferably a radical of vegetable origin, such as the behenyl radical.

The terpolymers used according to the invention are generally in aqueous dispersion.

An example of the terpolymer is the terpolymer obtained from acrylic acid, from methyl acrylate and from the compound of formula (III) where p is 40 and R2 is the behenyl radical. It is the methacrylic acid/methyl acrylate/dimethyl-m-isopropenylbenzyl isocyanate of behenyl alcohol ethoxylated with 40 EO, i.e., comprising 40 oxyethylene groups, terpolymer.

The acrylic terpolymer is present in the compositions of the invention in a concentration as active material of at most 0.5% by weight with respect to the total weight of the composition. The concentration as active material of terpolymer preferably ranges from 0.01 to 0.5% by weight and better still from 0.15 to 0.3% by weight with respect to the total weight of the composition. These ranges include all specific values and subranges therebetween, such as 0.02, 0.05, 0.1, 0.2 and 0.4% by weight.

In the composition according to the invention, the terpolymer/oily phase ratio preferably ranges from 1/30 to 1/100 and better still from 1/50 to 1/100. These ranges include all specific values and subranges therebetween, such as 1/40, 1/60, 1/75, 1/80, 1/90 and 1/95.

According to a specific embodiment of the invention, the composition of the invention does not comprise polymers other than the terpolymer.

The oily phase of the composition according to the invention generally represents from 1 to 30% and preferably from 10 to 25% by weight with respect to the total weight of the composition. These ranges include all specific values and subranges therebetween, such as 2, 5, 8, 12, 15 and 20% by weight.

The nature of the oily phase of the emulsion according to the invention is not critical, and may vary widely. The oily phase can thus be composed of any fatty substance and in particular oils conventionally used in the cosmetics or dermatological fields.

Examples of the oils which can be used in the emulsion of the invention, include vegetable oils, such as jojoba oil, avocado oil, sweet almond oil, apricot oil, maize oil and the liquid fraction of karite butter; mineral oils, such as liquid petrolatum; synthetic oils, such as 2-ethylhexyl palmitate, isopropyl myristate, hydrogenated isoparaffin, isononyl isononanoate or cetearyl octanoate; volatile or non-volatile silicone oils; and fluorinated oils. Other fatty substances capable of being present in the oily phase can be, for example, fatty acids, fatty alcohols, waxes and essential oils.

According to a specific embodiment of the invention, the composition of the invention comprises at least one silicone oil, preferably a volatile silicone oil, which can be chosen, for example, from cyclic or linear polydimethylsiloxanes and their mixtures. The cyclic polydimethylsiloxanes or cyclomethicones comprise from approximately 3 to 9 silicon atoms and preferably from 4 to 6 silicon atoms and can be, for example, cyclohexadimethylsiloxane and cyclopentadimethylsiloxane. The volatile linear polydimethylsiloxanes preferably comprise from approximately 3 to 9 silicon atoms. The volatile linear polydimethylsiloxanes generally have a viscosity at 25° C. of less than or equal to 5 cSt, whereas the cyclomethicones generally have a viscosity at 25° C. of less than or equal to 10 cSt.

The composition according to the invention comprises a physiologically acceptable medium, that is to say compatible with the skin, lips, scalp, eyes and/or hair.

As will be readily appreciated by those skilled in the art, the compositions of the invention can comprise adjuvants usual in the fields under consideration, such as hydrophilic or lipophilic active principles, preservatives, antioxidants, fragrances, solvents, fillers, screening agents, colouring materials, basic agents (triethanolamine, sodium hydroxide), acidic agents and lipid vesicles. These adjuvants are used in the proportions usual in the cosmetics field, for example from 0.01 to 30% of the total weight of the emulsion, and they are, depending on their nature, introduced into the aqueous phase or into the oily phase of the emulsion or into vesicles. These adjuvants and their concentrations must be such that they do not modify the property desired for the emulsion.

According to a specific form of the invention, the composition of the invention can be devoid of metal oxide nanopigments.

Examples of solvents, include linear or branched monoalcohols having from 1 to 8 carbon atoms, such as ethanol, propanol, butanol, isopropanol or isobutanol; polyethylene glycols having from 6 to 80 ethylene oxides; or polyols, such as propylene glycol, isoprene glycol and butylene glycol.

Examples of active principles, include moisturizers, such as polyols, for example glycerol and sorbitol; keratolytic agents; depigmenting agents; slimming agents and any active principle appropriate for the final aim of the composition.

The composition of the invention preferably exhibits a pH which has respect for the skin and which is compatible with the terpolymers used. The pH of the composition generally ranges from 6.5 to 8, preferably from 7 to 7.5. These ranges for the pH include all specific values and subranges therebetween, such as 6.6, 6.75, 7.1, 7.25 and 7.4.

The compositions according to the invention can be provided, for example, in the form of a serum or milk and are prepared according to the usual methods. They have the advantage of being vaporizable, which means that they are fluid enough to be applied by means of a vaporizer, which is devoid of propellant gas, is equipped with a pump of pump-action spray type, operates at atmospheric pressure and delivers the composition in the form of fine droplets.

The compositions which are the subject-matter of the invention find their application in particular in a large number of cosmetic treatments of the skin, lips and hair, including the scalp, in particular for caring for, removing make-up from, cleansing and/or scenting the skin, lips and/or hair.

The compositions according to the invention can be more particularly used as care and/or cleansing products for the face or as scented products for the skin.

A further subject-matter of the invention is consequently the cosmetic use of the composition as defined above for caring for, removing make-up from, cleansing and/or scenting the skin, lips and/or hair.

A final subject-matter of the invention is a process for the cosmetic treatment of the skin, including the scalp, hair and/or lips, characterized in that a composition as defined above is applied to the skin, hair and/or lips.

The compositions according to the invention can also be used for impregnating fabrics (woven and nonwoven) constituting cleansing wipes or towelettes intended for cleansing and/or removing make-up from the skin, eyelashes and/or lips. The woven or nonwoven fabric can be composed of natural or synthetic fibres and, for example, of cotton, polyamide, polyethylene, polyester, acrylic polymer, rayon, silk or paper.

Another subject-matter of the invention is therefore a cleansing wipe obtained by impregnating a fabric with a composition as defined above.

Another subject-matter of the invention is the use of the composition as defined above in the preparation of a cleansing wipe intended for removing make-up from and/or cleansing the skin, lips and/or eyelashes.

EXAMPLES

Having generally described this invention, a further understanding can be obtained by reference to certain specific examples which are provided herein for purposes of illustration only and are not intended to be limiting unless otherwise specified. The amounts shown are as % by weight, except when otherwise mentioned.

Example 1

| Vaporizable Ultrafluid Emulsion | |
|---|---|
| Phase A | |
| Methacrylic acid/methyl acrylate/dimethyl-m-isopropenylbenzyl isocyanate of behenyl alcohol ethoxylated with 40 EO terpolymer, as a 24% aqueous dispersion | 1.25% (i.e. 0.3% of active material) |
| Sodium hydroxide | 0.06% |
| Preservatives | 0.2% |
| Gycerol | 4% |
| Demineralized water | q.s. for 100% |
| Phase B | |
| Apricot oil | 15% |
| Cyclomethicone (cyclopentasiloxane) | 7% |
| Fragrance | 0.15% |

PROCEDURE

The sodium hydroxide is added to the polymer with stirring and the emulsion is prepared by pouring the phase B into the phase A with stirring. Homogenization is subsequently carried out under pressure (500 bar).

A very fluid emulsion is obtained which is particularly suitable for caring for the face in the case of greasy skin. The viscosity of the emulsion is 0.08 Pa·s (0.8 poises) on a Rheomat 180 equipped with a measuring body of 2 rotor, anchor type. It is also possible to use the emulsion as a moisturizing product for the body and as a slimming product with local vaporization.

Example 2

| Spray Ultrafluid Fragrance Mist | |
|---|---|
| Phase A | |
| Methacrylic acid/methyl acrylate/dimethyl-m-isopropenylbenzyl isocyanate of behenyl alcohol ethoxylated with 40 EO terpolymer, as a 24% aqueous dispersion | 1.25% (i.e. 0.3% of active material) |
| Sodium hydroxide | 0.06% |
| Preservatives | 0.2% |
| Gycerol | 4% |
| Demineralized water | q.s. for 100% |
| Phase B | |
| Jojoba oil | 7% |
| Cyclomethicone (cyclopentasiloxane) | 12% |
| Fragrance | 3% |

The procedure is identical to that of Example 1.

A very fluid emulsion is obtained having a viscosity of 0.1 Pa·s (1 poise) which is particularly suitable for scenting the body. Its penetration is instantaneous and does not leave a greasy film on the skin.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-03319, filed on Mar. 17, 1999, and incorporated herein by reference in its entirety.

What is claimed is:

1. A fluid composition in the form of an oil-in-water emulsion comprising, in a physiologically acceptable medium, an oily phase dispersed in an aqueous phase, comprising up to 0.5% by weight of active material with respect to the total weight of the composition of at least one acrylic terpolymer obtained from
    (a) an $\alpha,\beta$-ethylenically unsaturated carboxylic acid,
    (b) a non-surface-active ethylenically unsaturated monomer other than (a), and
    (c) a non-ionic urethane monomer which is the reaction product of a monohydric non-ionic amphiphilic compound with a monoethylenically unsaturated isocyanate.

2. The composition of claim 1, which is devoid of surfactant.

3. The composition of claim 1, wherein the acrylic terpolymer comprises, with respect to the total weight of the terpolymer:
    (a) approximately from 20 to 70% by weight of (a) and of a carboxylic acid comprising $\alpha,\beta$-ethylenic unsaturation,
    (b) approximately from 20 to 80% by weight of (b) and of a non-surface-active monomer comprising ethylenic unsaturation other than (a), and
    (c) approximately from 0.5 to 60% by weight of (c) of a non-ionic urethane monomer which is the reaction product of a monohydric non-ionic amphiphilic compound with an isocyanate comprising monoethylenic unsaturation.

4. The composition of claim 1, wherein (a) is selected from the group consisting of acrylic acid, methacrylic acid, crotonic acid, itaconic acid and maleic acid.

5. The composition of claim 1, wherein (a) is methacrylic acid.

6. The composition of claim 1, wherein(b) is selected from the group consisting of $C_1$–$C_4$ alkyl acrylates and methacrylates, styrene, vinyltoluene, vinyl acetate, acrylonitrile and vinylidene chloride.

7. The composition of claim 1, wherein(b) is methyl acrylate or ethyl acrylate.

8. The composition of claim 1, wherein the monohydric non-ionic amphiphilic compound used in order to obtain the non-ionic urethane monomer is a compound having the following formula (I):

$$R-(OCH_2CHR')_m-(OCH_2CH_2)_n-OH \qquad (I)$$

in which R is chosen from alkyl groups comprising from 6 to 30 carbon atoms and aralkyl groups comprising from 8 to 30 carbon atoms, R' is chosen from alkyl groups comprising from 1 to 4 carbon atoms, n is a mean number ranging from approximately 6 to 150 and m is a mean number ranging from approximately 0 to 50, provided that n is at least as great as m and that n+m=6 to 150.

9. The composition of claim 8, wherein R is selected from the group consisting of alkyl groups comprising from 18 to 26 carbon atoms and alkylphenyl groups in which the alkyl part comprises from 8 to 13 carbon atoms; the R' group is the methyl group; m=0 and n=6 to 150.

10. The composition of claim 1, wherein(c) is $\alpha,\alpha$-dimethyl-m-isopropenylbenzyl isocyanate.

11. The composition of claim 1, wherein the acrylic terpolymer is obtained by copolymerization in aqueous dispersion from methacrylic acid, as component (a), from methyl acrylate, as component (b), and from a non-ionic urethane macromonomer having the following structure (III):

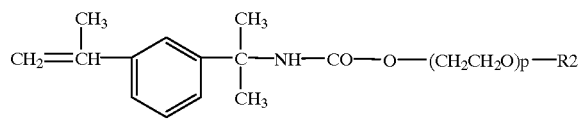

(III)

in which p ranges from 6 to 150 and R2 is chosen from linear alkyl radicals comprising from 18 to 26 and preferably from 20 to 24 carbon atoms, as component (c).

12. The composition of claim 1, wherein the terpolymer is present in a concentration as active material ranging from 0.01 to 0.5% by weight with respect to the total weight of the composition.

13. The composition of claim 1, wherein the oily phase represents from 1% to 30% by weight with respect to the total weight of the composition.

14. The composition of claim 1, which comprises at least one volatile silicone oil.

15. The composition of claim 1, which has pH of 6.5 to 8.

16. A method of caring for, removing make-up from, cleansing and/or scenting the skin, lips and/or hair, comprising applying the composition of claim 1 to the skin, lips and/or hair.

17. A cleansing wipe comprising a fabric impregnated with the composition of claim 1.

18. A method of making the cleansing wipe of claim 17, comprising impregnating a fabric with said composition.

19. A method of cosmetically treating the skin, hair and/or lips, comprising applying the composition of claim 1 to the skin, hair and/or lips.

20. The composition of claim 1, wherein (a) is present in an amount from 25 to 55% by weight, (b) is present in an amount from 30 to 65% by weight, and (c) is present in an amount from 10 to 50% by weight.

* * * * *

UNITED STATES PATENT AND TRADEMARK OFFICE
CERTIFICATE OF CORRECTION

PATENT NO. : 6,245,322 B1
DATED : June 12, 2001
INVENTOR(S) : Pascal Simon

Page 1 of 1

It is certified that error appears in the above-identified patent and that said Letters Patent is hereby corrected as shown below:

<u>Column 8,</u>
Line 23, delete "and";
Line 27, delete "and";
Line 40, "wherein(b)" should read -- wherein (b) --;
Line 44, "wherein(b)" should read -- wherein (b) --.

Signed and Sealed this

Ninth Day of April, 2002

Attest:

Attesting Officer

JAMES E. ROGAN
*Director of the United States Patent and Trademark Office*